United States Patent
Pung et al.

(10) Patent No.: US 12,076,260 B2
(45) Date of Patent: *Sep. 3, 2024

(54) METHOD AND APPARATUS FOR STENT DELIVERY

(71) Applicant: MicroVention, Inc., Aliso Viejo, CA (US)

(72) Inventors: Ponaka Pung, Signal Hill, CA (US); Helen Nguyen, Garden Grove, CA (US)

(73) Assignee: MicroVention, Inc., Aliso Viejo, CA (US)

(*) Notice: Subject to any disclaimer, the term of this patent is extended or adjusted under 35 U.S.C. 154(b) by 502 days.

This patent is subject to a terminal disclaimer.

(21) Appl. No.: 16/910,400

(22) Filed: Jun. 24, 2020

(65) Prior Publication Data
US 2020/0315828 A1    Oct. 8, 2020

Related U.S. Application Data

(63) Continuation of application No. 15/725,142, filed on Oct. 4, 2017, now Pat. No. 10,722,392.
(Continued)

(51) Int. Cl.
*A61F 2/966*  (2013.01)
*A61F 2/01*  (2006.01)
(Continued)

(52) U.S. Cl.
CPC .............. *A61F 2/966* (2013.01); *A61F 2/013* (2013.01); *A61F 2/90* (2013.01);
(Continued)

(58) Field of Classification Search
CPC .. A61F 2/966; A61F 2/90; A61F 2/013; A61F 2/852; A61F 2002/9534; A61F 2002/9665; A61F 2002/011
See application file for complete search history.

(56) References Cited

U.S. PATENT DOCUMENTS 6,168,621 B1    1/2001   Vrba
6,511,496 B1    1/2003   Huter et al.
(Continued)

FOREIGN PATENT DOCUMENTS

CN       104042376 A       9/2014
JP       2010-521264 A     6/2010
(Continued)

OTHER PUBLICATIONS

Japanese Patent Office, Office Action dated Jul. 20, 2021 with English translation in Japanese Patent Application No. 2019-518270, 5 pages.
(Continued)

*Primary Examiner* — Katherine M Shi
(74) *Attorney, Agent, or Firm* — Inskeep IP Group, Inc.

(57) ABSTRACT

Disclosed is a method, apparatus, and kit for assisting the expansion of a self-expanding stent, especially within highly curved or tortuous blood vessels. An elongated pusher having an expandable distal mesh portion can be positioned within a self-expanding stent, expanding during delivery to provide extra expansion force to the stent to ensure the stent properly expands.

11 Claims, 9 Drawing Sheets

Related U.S. Application Data

(60) Provisional application No. 62/404,102, filed on Oct. 4, 2016.

(51) Int. Cl.
*A61F 2/90* (2013.01)
*A61F 2/82* (2013.01)
*A61F 2/88* (2006.01)

(52) U.S. Cl.
CPC ... *A61F 2002/016* (2013.01); *A61F 2002/018* (2013.01); *A61F 2002/828* (2013.01); *A61F 2/88* (2013.01); *A61F 2230/0013* (2013.01); *A61F 2250/0015* (2013.01); *A61F 2250/0023* (2013.01); *A61F 2250/0098* (2013.01)

(56) References Cited

U.S. PATENT DOCUMENTS

| | | | |
|---|---|---|---|
| 6,558,405 B1 | 5/2003 | McInnes | |
| 6,656,219 B1 | 12/2003 | Wiktor | |
| 6,964,673 B2 | 11/2005 | Tsugita et al. | |
| 7,763,011 B2 | 7/2010 | Ortiz et al. | |
| 8,048,139 B2 | 11/2011 | Frid et al. | |
| 8,679,150 B1 | 3/2014 | Janardhan et al. | |
| 8,814,925 B2 | 8/2014 | Hilaire et al. | |
| 9,060,777 B1 | 6/2015 | Wallace et al. | |
| 9,439,791 B2 | 9/2016 | Vong et al. | |
| 9,867,725 B2 | 1/2018 | Tieu et al. | |
| 2002/0087186 A1 | 7/2002 | Shelso | |
| 2004/0230284 A1 | 11/2004 | Headley et al. | |
| 2005/0228438 A1 | 10/2005 | Sachar et al. | |
| 2006/0025843 A1* | 2/2006 | Gurm | A61F 2/954 623/1.11 |
| 2007/0225792 A1* | 9/2007 | Granada | A61F 2/958 623/1.11 |
| 2009/0326640 A1* | 12/2009 | Yoshimura | A61F 2/966 112/475.08 |
| 2010/0023113 A1 | 1/2010 | Frid | |
| 2011/0082490 A1 | 4/2011 | Connelly et al. | |
| 2012/0259404 A1 | 10/2012 | Tieu | |
| 2014/0046428 A1 | 2/2014 | Cragg et al. | |
| 2014/0081380 A1 | 3/2014 | Giasolli et al. | |
| 2014/0200648 A1* | 7/2014 | Newell | A61F 2/844 623/1.11 |
| 2014/0276778 A1 | 9/2014 | McLawhorn et al. | |
| 2015/0133989 A1 | 5/2015 | Lubock et al. | |
| 2015/0297382 A1* | 10/2015 | Tassoni, Jr. | A61F 2/966 623/1.12 |
| 2015/0374483 A1* | 12/2015 | Janardhan | B23K 26/1435 606/200 |
| 2016/0193061 A1 | 7/2016 | Newell et al. | |

FOREIGN PATENT DOCUMENTS

| | | |
|---|---|---|
| WO | WO 2008/012285 A1 | 1/2008 |
| WO | WO2008/113857 A2 | 9/2008 |
| WO | WO2008/113857 A3 | 9/2008 |
| WO | WO 2011/025887 A1 | 3/2011 |
| WO | WO 2015/160721 A1 | 10/2015 |
| WO | WO 2015/184075 A1 | 12/2015 |

OTHER PUBLICATIONS

European Patent Office, Supplementary Extended European Search Report dated Apr. 21, 2020 in European Patent Application No. 17859132.7, 8 pages.
WIPO, U.S. International Search Authority, International Search Report and Written Opinion dated Dec. 4, 2017 in International Patent Application No. PCT/US2017/055183, 10 pages.
Chinse Patent Office, Office Action dated Jun. 6, 2022 with English translation in Chinese Patent Application No. 2017800706914, 12 pages.
China National Intellectual Property Administration, Third Office Action dated Dec. 2, 2022 with English translation in Chinese Patent Application No. 2017800706914, 15 pages.
Japanese Patent Office, Office Action dated Oct. 17, 2023 with English translation in Japanese Patent Application No. 2022-186244, 7 pages.
Japan Patent Office, Official Action dated Jul. 2, 2024 in Japanese Patent Application No. 2022-186244 with English translation, 5 pages.

* cited by examiner

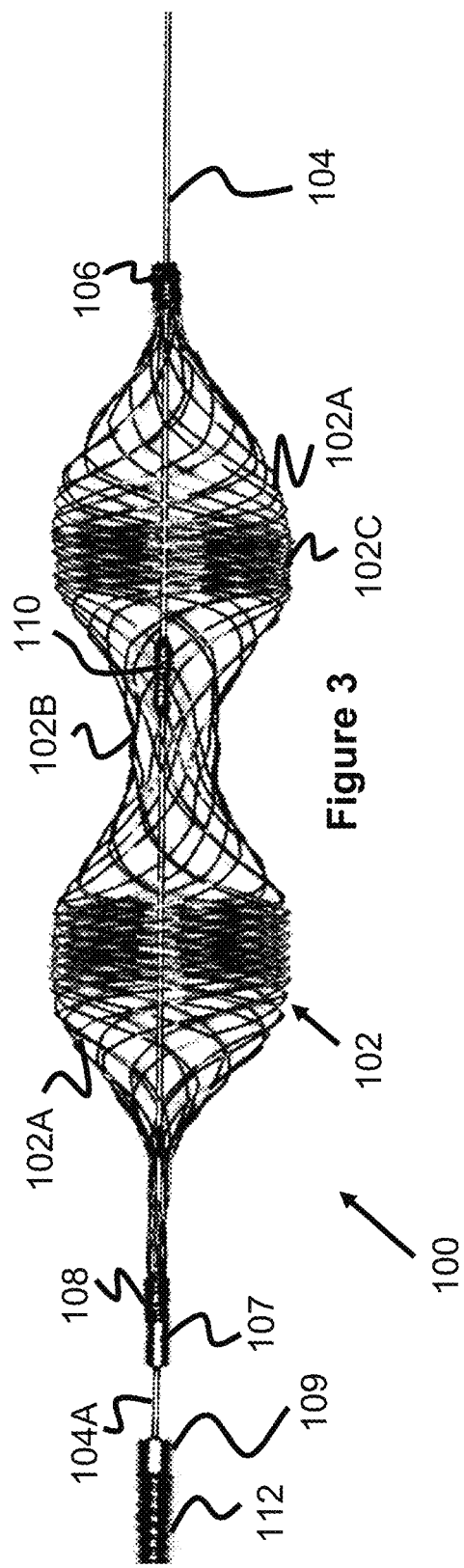
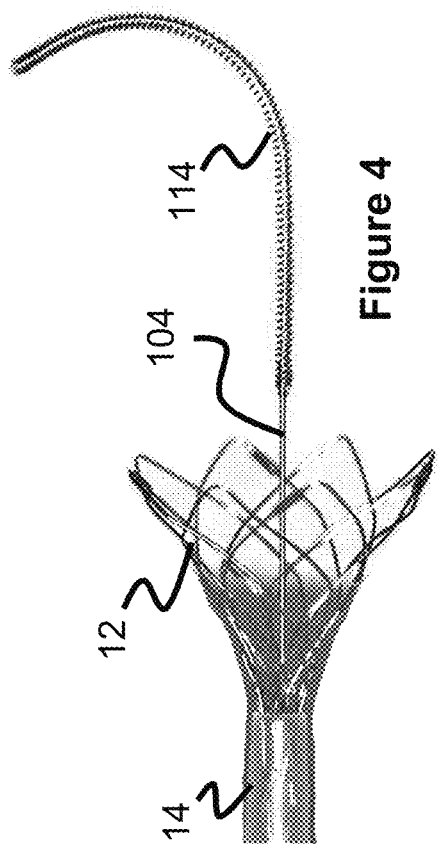
Figure 3
Figure 4

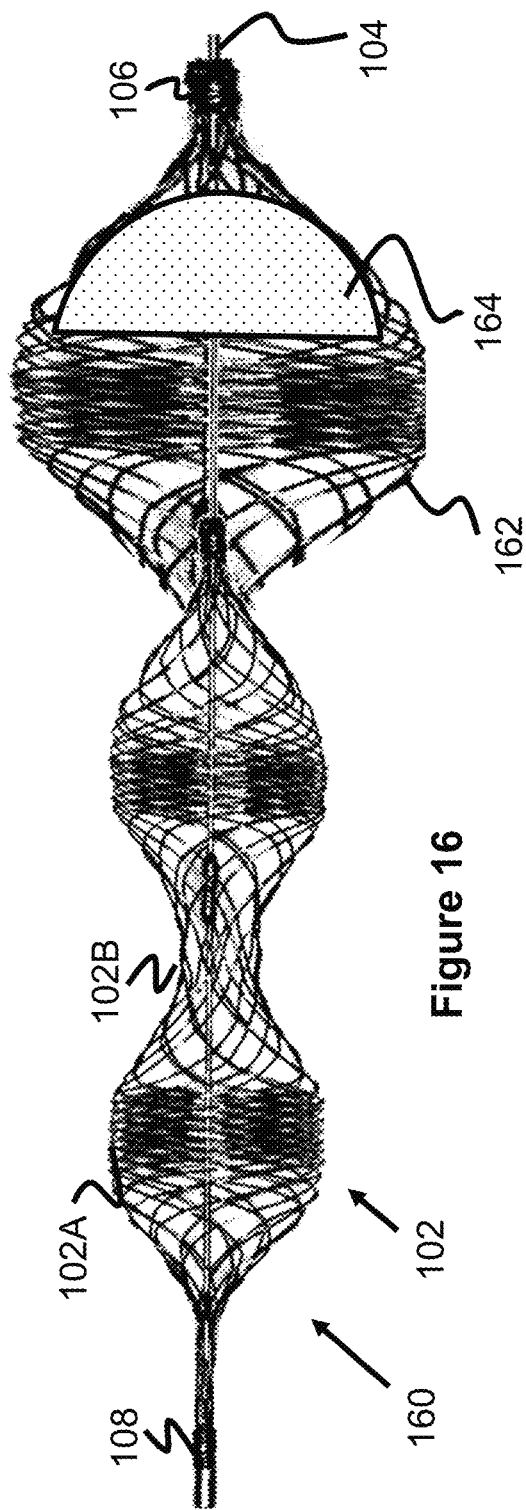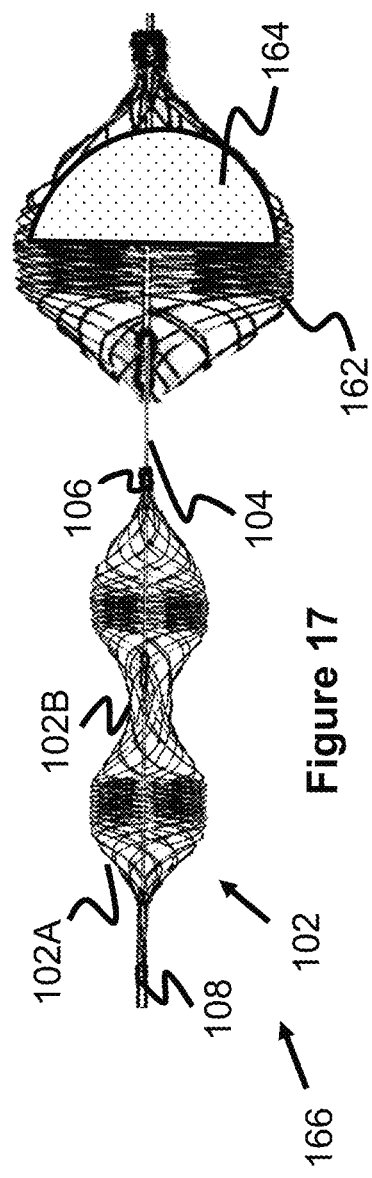
Figure 16
Figure 17

METHOD AND APPARATUS FOR STENT DELIVERY

RELATED APPLICATIONS

This application is a continuation of and claims priority to U.S. patent application Ser. No. 15/725,142 filed Oct. 4, 2017 entitled Method And Apparatus For Stent Delivery, which claims benefit of and priority to U.S. Provisional Application Ser. No. 62/404,102 filed Oct. 4, 2016 entitled Methods For Delivering and Using a Stent, both of which are hereby incorporated herein by reference in their entireties.

BACKGROUND OF THE INVENTION

Typically, stents are tubular devices that are delivered into a patient's vascular system via a catheter or similar delivery device. Stents can be used to treat a variety of different conditions, including stenosis and aneurysms. When used to treat stenosis (narrowing of a vessel), the stent is used to press against thrombus and open a vessel to allow normal blood flow. When used to treat aneurysms, low-porosity stents can be used to limit blood flow to a vessel (so-called flow-diversion stents) to promote clotting of the aneurysm and reduce the risk of aneurysm rupture. Alternatively, the stent can be used as a scaffold to keep other embolic material (such as embolic coils) within the aneurysm.

When a stent is deployed in a generally linear portion of a vessel, stent delivery is typically straightforward. For example, a distal end of a delivery catheter is advance near a desired delivery location and the outer sheath is withdrawn, allowing the stent to expand within the vessel. Even in these linear vessel situations though, stent delivery can still be challenging due to variables such as the size of the stent, size of the delivery catheter, and size of the vessel. Often, when the stent must be deployed at or near a tortuous or heavily curved portion of a vessel, a self-expanding stent may have difficulty properly deploying. For example, FIG. 1 illustrates a self-expanding stent 12 (e.g., such as that described in U.S. Pat. No. 9,439,791, incorporated herein by reference in its entirety) being deployed in a heavily curved portion of a vessel 10. While the catheter 14 releases the stent 12, it forms a flat or collapsed portion 12A against the outer curved surface of the vessel 10. FIG. 2 illustrates a second flat or collapsed portion 12A formed against the outer surface of a second curve of the vessel 10 as the stent 12 is further expanded. When collapsed portions 12A occur, the physician's only alternative is to attempt to rotate the catheter 14 and/or partially retract and re-deploy the stent 12.

SUMMARY OF THE INVENTION

The present invention is directed to a method, apparatus, and kit for assisting the expansion of a self-expanding stent, especially within highly curved or tortuous blood vessels.

One embodiment is directed to a stent delivery device comprising an elongated pusher having a self-expanding mesh portion at its distal end. The mesh portion preferably includes one or more mesh bulbs connected to each other by a reduced-diameter region. Optionally, different areas of the mesh portion, such as a middle region of the bulbs, can have a more densely braided portion have a higher pic-per-inch.

In one embodiment, the mesh portion is disposed on a core wire that extends from a distal end of the pusher. The mesh portion can slide longitudinally on the core wire, a proximal end can be fixed to the core wire or pusher, or a distal end can be fixed to the core wire.

The mesh portion can contain one bulb portion or can contain a plurality of bulb portions (e.g., between 2 and 10 or more). Further the bulb portions can have a variety of different shapes, such as spherical, spheroid, elongated cylindrical, conical, or diamond shape.

In one embodiment the core wire can terminate at the distal end of the pusher or partway within the first bulb portion. By not extending all the way through the mesh portion, the assistance device may be more flexible to accommodate a higher degree of vessel curvature.

In one embodiment, structural wire members extend between bulbs and over the reduced diameter region. These structural wire members help capture clots or other debris dislodged during a stent delivery procedure.

In one embodiment, a distal protection device is included at the distal end of the device. The distal protection device can include a relatively larger expandable mesh bulb containing a filter or similar structure to catch any material dislodged during stent deployment. The distal protection device can be braided integrally with the mesh portion or can be a separate structure connected near a distal end of the core wire.

The present invention is also directed to a method of deploying a stent, comprising exposing a distal portion of a stent within a curved region of a vasculature, expanding the mesh portion of a stent assistance device within the stent so as to apply radial expansion force to an interior of the stent, fully deploying the stent, and then withdrawing the stent assistance device.

The present invention is also directed to a kit comprising a catheter, a pusher within the catheter, a self-expanding mesh portion attached to a distal end of the pusher, and a stent disposed over the mesh portion.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 3 illustrates one embodiment of a stent assistance device in an expanded configuration, according to the present invention.

FIG. 4 illustrates a distal end of the stent assistance device of FIG. 3 within a stent, according to the present invention.

FIG. 16 illustrates a stent assistance device having a distal protection device attached to its mesh portion, according to the present invention.

FIG. 17 illustrates a stent assistance device having a distal protection device separate from its mesh portion, according to the present invention.

DESCRIPTION OF EMBODIMENTS

Figure 1:
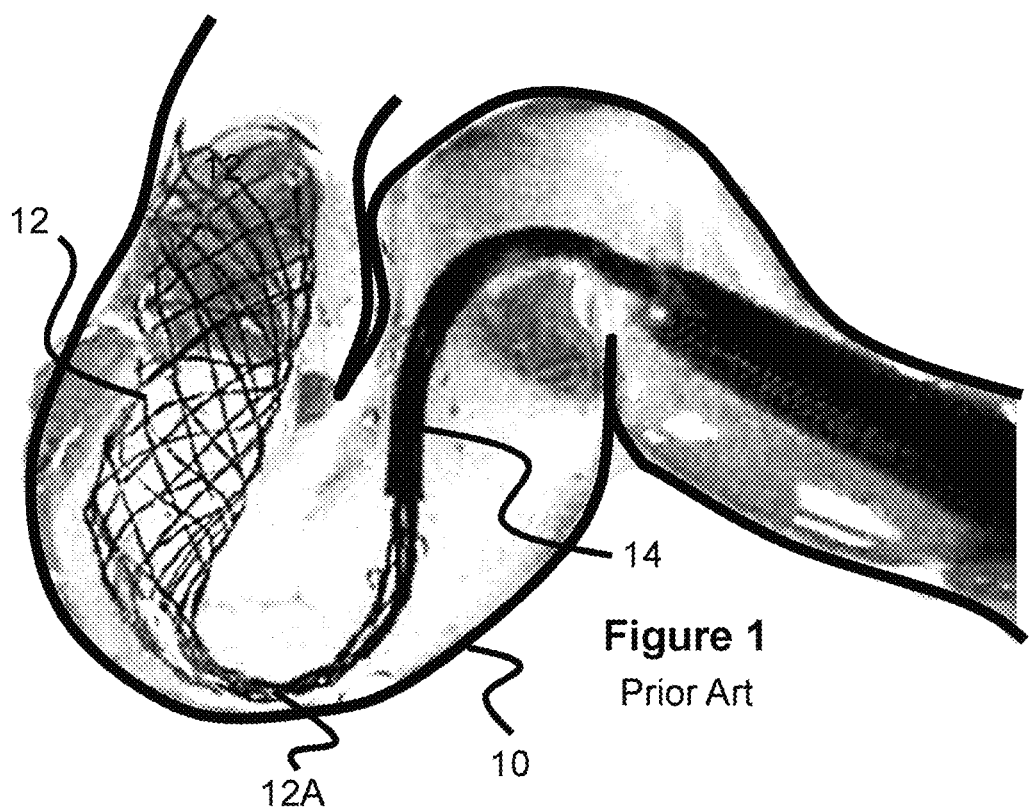
FIG. 1 illustrates a stent being deployed in a tortuous portion of a blood vessel.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 2:
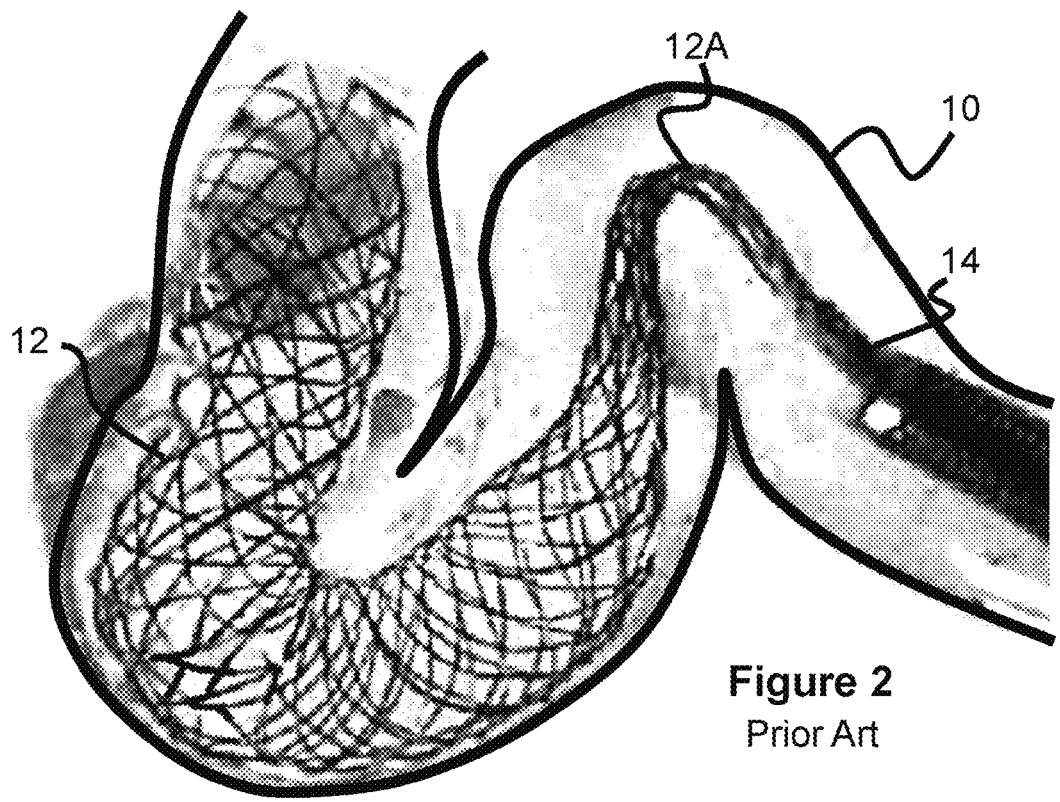
FIG. 2 illustrates the stent of FIG. 1 being further deployed in the tortuous portion of the blood vessel.

The present invention is generally directed to devices that can be expanded within an interior passage of a self-expanding stent 12 during deployment to provide additional expansion force that helps the stent 12 radially expand and to maintain that radially expanded state. This added expansion force can be particularly helpful in highly tortuous vessels 10 that tend to force the stent 12 to form collapsed portions 12A, as shown and discussed with regard to FIGS. 1 and 2.

Please note for FIG. 3 and onwards, unless indicated otherwise, anything to the right in the Figures is considered distal (in the direction of the patient/patient vasculature) while anything to the left in the Figures is considered proximal (in the direction away or outside of the patient/patient vasculature).

FIG. 3 illustrates an expandable stent assistance device 100 according to one embodiment of the present invention. The stent assistance device 100 can be thought of as the distal part of a broader delivery system or pusher used to mechanically push or mechanically deliver a stent 12. The stent assistance device 100 includes a pusher body 112 having an elongated cylindrical shape culminating with a radiopaque (e.g., tantalum) marker band 109 and a stationary or fixed core wire 104 which is exposed distal to pusher body 112.

In one embodiment, the core wire spans a lumen of pusher body 112 where only a distal section of core wire 104 is exposed. In another embodiment, core wire 104 is attached to a distal end of pusher body 112. The core wire 104 includes a fixed radiopaque marker band 107. In one example, the stent 12 can include a number of proximally placed flared ends or loops with enlarged marker coil regions and one or more of the flared end or loops sit within marker bands 109 and 107—at location 104A—to hold the stent during delivery. The enlarged marker coil region maintains the stent flare/loop pinned between marker bands 107 and 109. Marker bands 107, 109 may be sized about 0.0135 inches in diameter while core wire 104 is about 0.003 inches in diameter. The stent adopts a first, collapsed configuration when sheathed within a delivery catheter 14—best shown in FIGS. 4-5. When the pusher body 112 is pushed past the distal end of the catheter 14 or when catheter 14 is retracted, the stent expands to its heat-set expansile shape. When the stent is fully pushed from the catheter 14 the pinned stent loops/flares will expand such that they are no longer held at location 104A. Similar stents and delivery systems/configurations can be seen in the previously incorporated U.S. Pat. No. 9,439,791.

The stent assistance device 100 further includes a mesh portion 102 which sits along core wire 104. The purpose of this mesh portion is to provide additional, outward radial force on the stent 12 to help the stent 12 expand and to maintain that expanded shape during the procedure. The mesh portion 102 is formed from a plurality of wires and is heat set into an expansile shape such that the mesh portion self-expands upon being freed from the overlying delivery catheter 14.

Preferably, the mesh portion 102 is braided and heat-set to form one or more bulbs 102A (e.g., 2 bulbs as shown in FIG. 3—or more bulbs are also possible), wherein each bulb is connected by a reduced diameter portion 102B. The mesh portion includes a number of crimp points (proximal crimp point 108, distal crimp point 106). The crimp points 106, 108 can be created by crimping the wire by itself, welding, adhering or by using a metal band (e.g., a radiopaque marker band). In various embodiments, the crimp points 106/108 can either float/slide over the core wire 104 or are fixed to the core wire 104, in a manner that will be explained below.

The mesh portion 102 can be woven in a variety of different configurations. For example, 12, 16, 24, 36, or 48 wires can be woven together in a 1×1, 1×2, or other wire configurations.

The porosity or size of the openings of the mesh portion 102 in its expanded configuration can vary over the length of the mesh portion 102. In the embodiment shown in FIG. 3, the radially centered portion 102C of the bulbs 102A have a lower porosity (i.e., a higher number of wires or higher pics-per-inch). This creates a stronger, more reinforced area of the mesh portion 102 that can potentially provide a higher outward radial force and be less likely to entangle with the wires of the stent 12 when the stent contacts mesh portion 102.

Other embodiments may have other parts of the mesh portion 102 strengthened in this manner, such as the ends of the bulbs 102A or the reduced diameter regions 102B. In one embodiment, the wires of the mesh portion 102 are comprised of nitinol and have a diameter of the range of about 0.001 to 0.0015 inches. Radiopaque (e.g. tantalum) wires may also be included in the mesh to augment visualization as well as to provide regions of increasing stiffness in the braid to further enhance the contact force against the overlying stent 12. Drawn-filled tubing with a nitinol jacket and tantalum core, or vice-versa, may also be used.

The mesh portion 102 can be created in a number of different ways. For instance, a mandrel with bulbed regions shaped similar to bulbs 102A and reduced diameter regions shaped similar to region 102B can be used to create the mesh portion shape. Either the wires can be woven on the mandrel and then heat set to impart the shapes, or a pre-woven mesh cylinder can be placed over the mandrel and heat set.

Alternatively, a mandrel with a consistent cylindrical diameter can be used, where the mesh portion is first woven over said mandrel. The mesh portion 102 is then be taken off of the mandrel and ties or marker bands are selectively applied at locations to create the reduced diameter regions 102B. A subsequent heat treatment is then be applied to impart the shape shown in, for instance, FIG. 3.

In one embodiment, core wire 104 maintains a fixed position relative to the other components of the pusher body 112. Crimp point 108 is fixed to core wire 104 while crimp point 106 slides or floats longitudinally over said core wire 104. Since braided mesh structures tend to foreshorten in length as they radially expand, the longitudinally slideable crimp point 106 allows the distal end of the mesh portion 102 to move proximally as it is exposed from the catheter 14 and begins to radially expand.

If a stent 12 is far oversized compared to the vessel, there is high radial force against the vessel wall which could cause the stent 12 to get stuck. This could also result in the mesh portion 102 becoming stuck, since it might also be oversized relative to the vessel and therefore may become stuck in the vessel or to the stent wires. To avoid scenarios where the mesh portion 102 becomes stuck in an expanded shape, the core wire can include a fixed marker band 110 between the two crimp points 106, 108 where fixed marker band 110 acts as a backstop to make sure crimp point 106 cannot foreshorten too far proximally.

Alternative embodiments are also possible, including configurations where either one of crimp point 106, 108 is fixed/slidable, or scenarios where crimp points 106, 108 are both fixed or both slidable. To enable a slidable crimp point, the crimp point inner diameter would have to be at least slightly larger than the core wire diameter. In one example the core wire would be about 0.003 inches in diameter while any sliding crimp point would have an inner diameter of about 0.005-0.006 inches. To create a fixed crimp point, in one example, a crimping tool, adhesive, or welding can be used to mechanically affix the crimp point to core wire 104.

Core wire 104 can be comprised of a nitinol wire. As seen best in FIG. 4, the distal end of core wire 104 includes a relatively soft distal tip 114, for example, that is composed of tantalum or platinum wire coiled around an underlying nitinol wire. The tantalum or platinum coiled wire would aid in visualization so that a user can tell where the distal end of wire 104 is positioned, while the coil would provide increased flexibility so that when portion 114 hits a vessel wall it will not get stuck against the vessel wall. The soft distal tip 114 can have a pre-set J-shape as shown in FIG. 4, or can be meldable such that a user can impart this J-shape over a provided mandrel. The angled J-shape is particularly useful in navigating the system through vessel bifurcations. This distal tip may eliminate the need for a separate guidewire to track the catheter and stent to the target treatment area.

Figure 5:
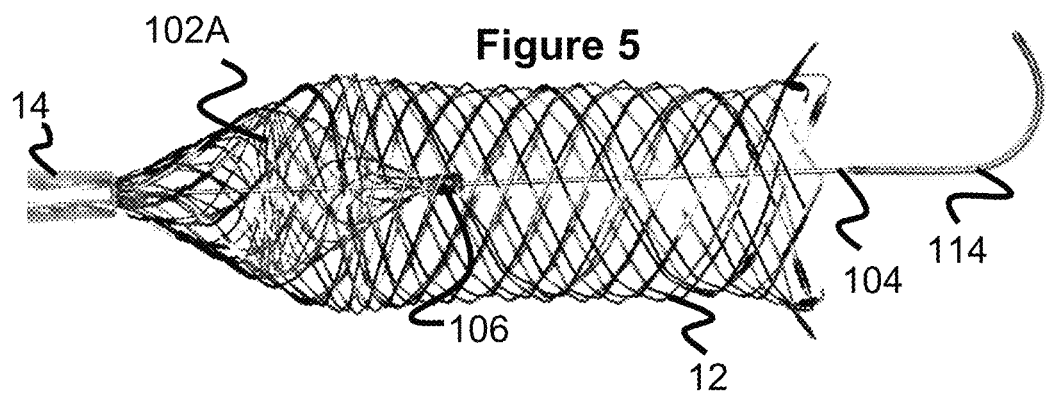
FIG. 5 illustrates the stent assistance device of FIG. 3 within a stent, according to the present invention.

FIGS. 4-5 generally show how the stent 12 would adopt its expanded configuration when delivered and how the mesh portion can aid in keeping the stent propped open. In FIG. 4, stent 12 is just being released from catheter 14 where the distal portion of the stent 12 is adopting its expanded shape. In FIG. 5, mesh portion 102A is expanded against the proximal part of stent 12 and helps keep the stent open by providing a scaffolding force against the proximal portion of stent 12. In FIG. 5, the mesh portion either utilizes only one bulb 102A, or the stent 12 is only partially deployed such that a limited amount of the stent is exposed which corresponds to only a distal part of the mesh portion 102.

Figure 6:
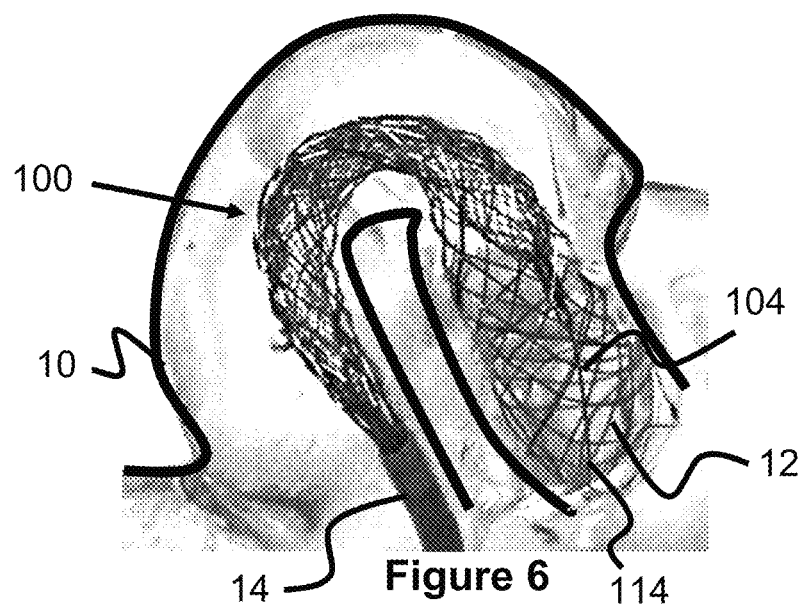
FIG. 6 illustrates the stent assistance device of FIG. 3 assisting deployment of a stent within a tortuous vasculature.
Figure 7:
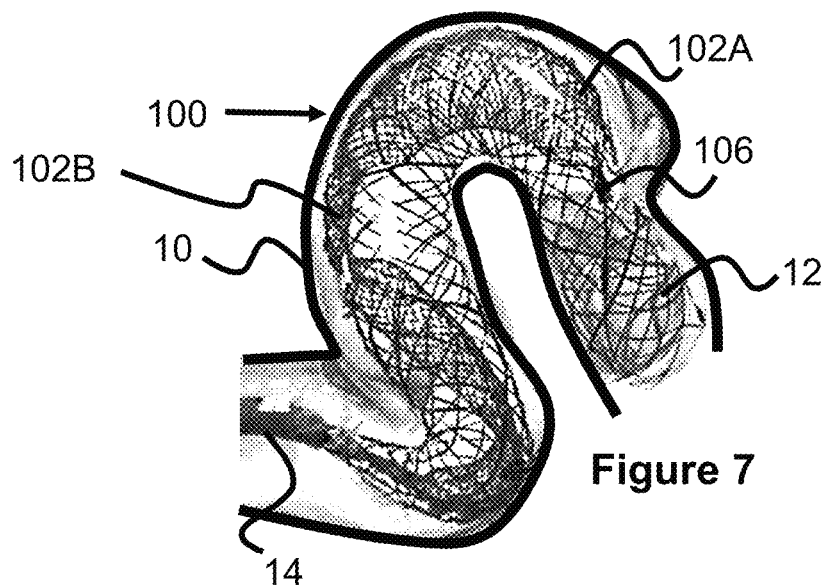
FIG. 7 illustrates the stent assistance device of FIG. 3 assisting further deployment of the stent of FIG. 6.

In operation, as seen in FIGS. 6 and 7, the distal end of the catheter 14 is advanced at or adjacent to the region that the physician desires to deploy the stent 12. The catheter 14 is then either retracted from the stent 12 or the stent 12 is pushed outwards from the catheter's internal passage. As the stent 12 is deployed around a curved portion of the patient's vessel 10, the mesh portion 102 and particularly the beads 102A radially expand and push outwardly from within the stent 12 propping the stent open as shown in FIG. 7.

Catheters often include a radiopaque marker band which is located 3 centimeters from their distal tip so that the user can line up a marker band located somewhere along the delivery pusher determine the location of the proximal end of a stent is. In this respect, the physician can judge when the stent is fully deployed or almost fully deployed based on the pusher's longitudinal position. FIG. 3 and the earlier description described marker band 109 which is connected to pusher body 112, and marker band 107 along core wire 104. Either of these markers can be aligned with the catheter 3-centimeter marker to determine that the stent is completely deployed or almost completely deployed. Once the stent 12 is fully deployed, pusher body 112 is proximally retracted, causing the mesh portion 102 to move back into the passage of the catheter 14.

In some embodiments, the core wire 104 is freely movable relative to the body of the pusher body 112. This movable core wire 104 can allow a physician to manually control the expansion and/or contraction of the mesh portion 102, depending on the configuration of the crimp points 106 and 108.

Figure 8:
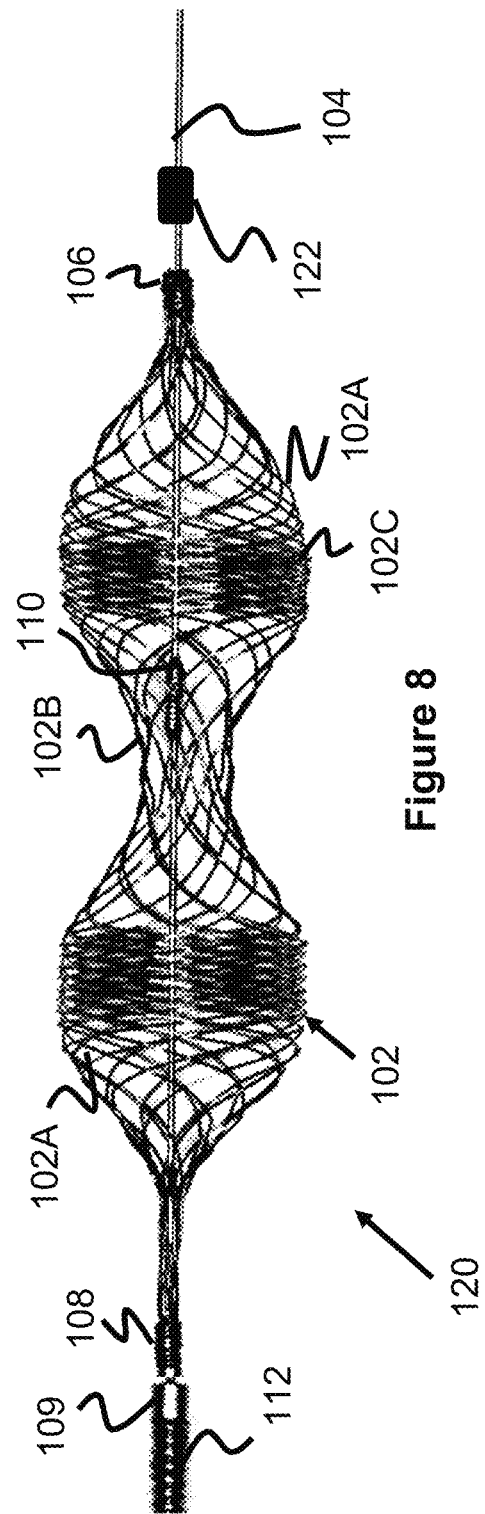
FIG. 8 illustrates another embodiment of a stent assistance device, according to the present invention.

For example, FIG. 8 shows such an embodiment of a stent assist device 120 in which the core wire 104 can move independently of pusher body 112 to selectively increase the radius of the mesh bulb portions 102A to augment the radial push force against the overlying stent 112. In this embodiment, pusher body 112 includes a lumen extending along its length and opening at its proximal and distal ends. The core wire 104 can be pushed and pulled independently of the pusher body 112 through this lumen, allowing the proximal end of core wire 104 to be manipulated independently of pusher body 112 by a user/physician.

Proximal crimp point 108 is fixed either to pusher body 112 or to core wire 104. If proximal crimp point 108 is fixed to core wire 104 (rather than fixed to pusher body 112), said proximal crimp point 108 is placed relatively close to the pusher body 112 such that when the core wire is retracted the crimp point will immediately abut pusher body 112, preventing any further proximal movement of mesh portion 102. Distal crimp point 106 is longitudinally movable over core wire 104. The core wire 104 includes another fixed distal marker band 122 which is distal of mesh crimp point 106, where said fixed distal marker band 122 is fixed to the core wire. When the user/physician retracts core wire 104, distal marker band 122 will contact crimp point 106 and since crimp point 106 can slide, this causes crimp point 106 to move proximally inwards which would increase the radial profile of mesh portion 102A as mesh portion 102 longitudinally contracts due to the push force supplied by distal marker 122. In this way, the user may selectively augment the radial expansion force applied to the stent by being able to independently control the diameter of mesh bulb 102A. Marker band 110, like in the embodiment of FIG. 3, provides a backstop surface to limit how much distal crimp point 106 can float.

Another alternative embodiment is similar to the device 120 of FIG. 8. However, in this embodiment, the pusher body 112 lumen is larger than crimp points 106, 108 such that all or part of mesh portion 102 can be retracted within pusher body 112 by proximally pulling the core wire 104. Proximal crimp point 108 can slide over core wire 108 while distal crimp point 106 is fixed to core wire 104. Retracting core wire 104 causes the proximal crimp point 108 to enter delivery pusher body 112. Further retraction of core wire 104 can cause mesh portion 102 to also enter pusher body 112 (the ability to do so would depend on how oversized the inner diameter of pusher body 112 is compared to mesh portion 102); however, even an ability to get the proximal part of mesh portion 102 within pusher body 112 would allow the user to customize how much of the mesh portion 102 would contact the overlying stent.

In one example, the core wire adopts a first, retracted configuration where all or a portion of mesh portion 102 is housed within pusher body 112. The user then delivers the stent 12, and if there are tracking issues where the stent 12 is stuck at a tortuous bend where a portion of the stent won't open, the user may then push the core wire distally so that the mesh portion 102 is exposed and the mesh bulb sections 102A contact the stent 12 to push it open. This is primarily enabled by the ability of proximal crimp point 108 to slide in this embodiment, since this will allow the mesh portion 102 to longitudinally expand and thus radially contract.

Alternatively, this functionality is also possible if proximal crimp point 108 is fixed to core wire 104 but distal crimp point 106 is slidable relative to core wire 104. In this arrangement, when core wire 104 is retracted within pusher body 112, the proximal crimp point 108 will enter pusher body 112 and then as more of the mesh portion 102 is retracted within pusher body 112, the mesh portion 102 will longitudinally expand pushing the slidable distal crimp 106 distally which in turn facilitates the continued radial contraction/longitudinal expansion of mesh portion 102. In contrast, if both crimp points 106, 108 were fixed, mesh portion 102 would have a relatively fixed shape and it would be difficult to get a radially compressed/longitudinally expanded shape to fit within pusher body 112.

Figure 9:
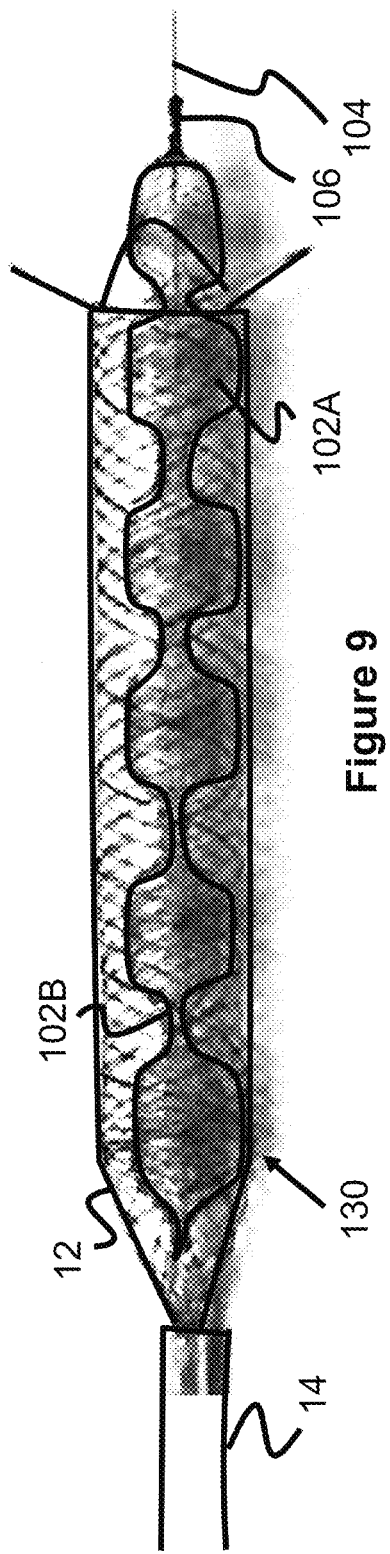
FIG. 9 illustrates another embodiment of a stent assistance device having a plurality of mesh bulbs, according to the present invention.

FIG. 9 illustrates a stent assistance device 130 that has six bulbs 102A instead of the two bulbs generally shown in the previous stent assistance device embodiments of the previous Figures. It is contemplated that many bulbs 102A can be included as part of the mesh portion (e.g., 1, 2, 3, 4, 5, 6, 7, 8, 9, or 10+ bulbs). The number, length, and diameter of these bulbs 102A may be selected to correspond to the length and expanded diameter of the particular stent 12 that it is being used with.

Figure 10:
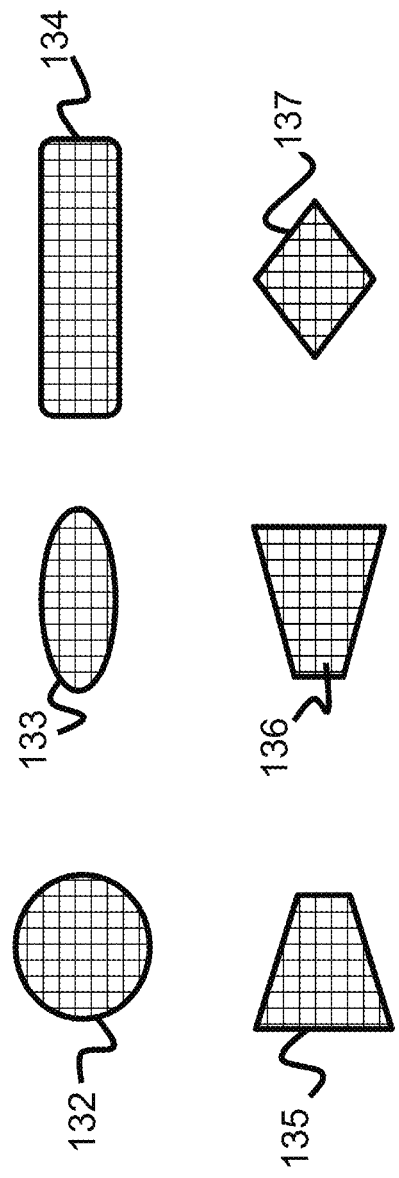
FIG. 10 illustrates a plurality of different possible shapes for the mesh bulbs of the present invention.
Figure 11:
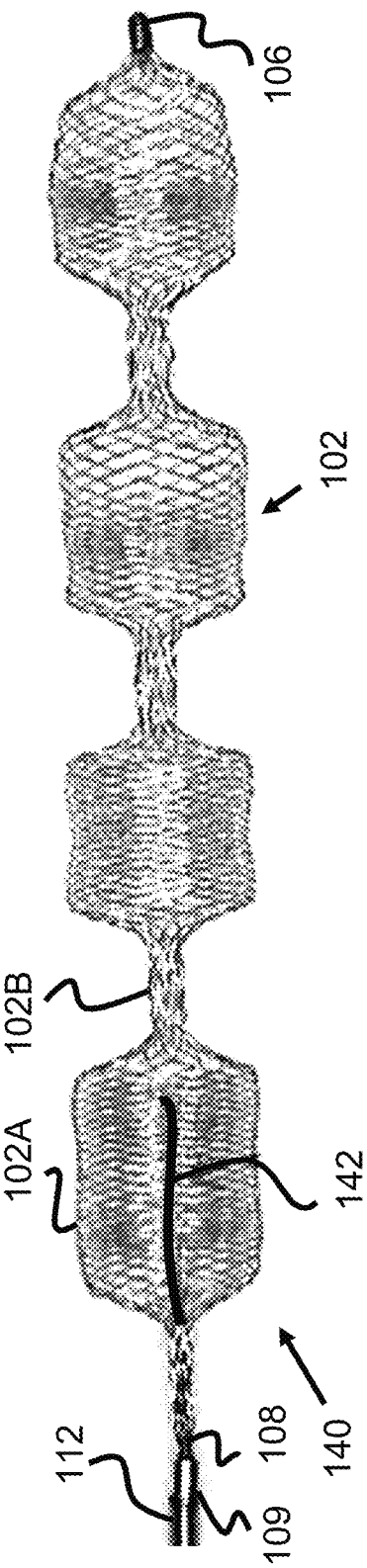
FIG. 11 illustrates another embodiment of a stent assistance device having a core wire that terminates within a proximal location of the mesh portion, according to the present invention.
Figure 12:
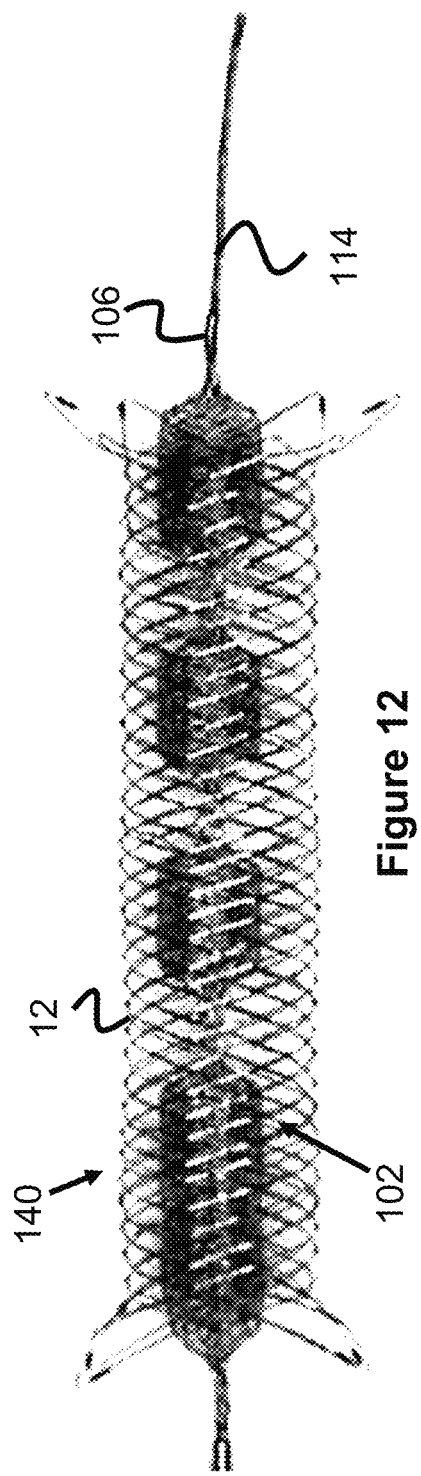
FIG. 12 illustrates the stent assistance device of FIG. 11 within a stent, according to the present invention.
Figure 13:
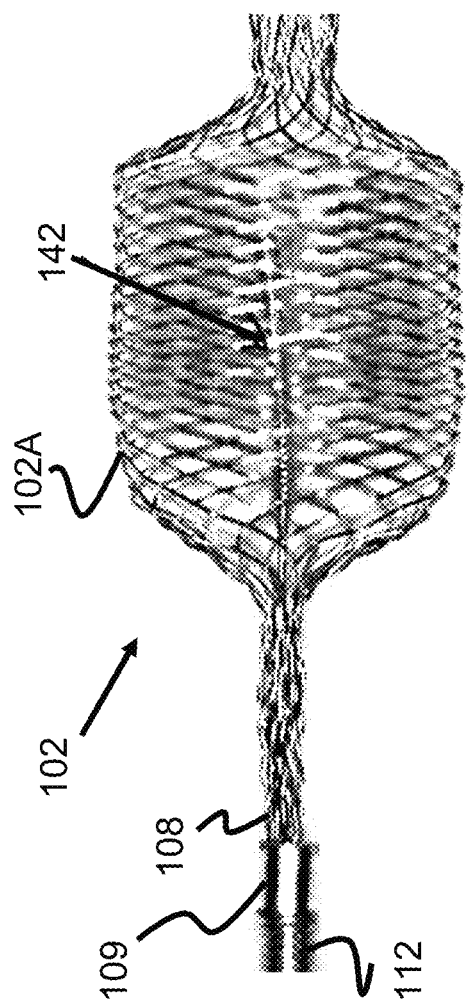
FIG. 13 illustrates a proximal bulb of the stent assistance device of FIG. 11, according to the present invention.

In addition to various numbers of bulbs 102A, the bulbs 102A can have a variety of different shapes (e.g., either all bulbs have the same shape or a mixture of shapes are present). FIG. 10 illustrates example bulb shapes that include a spherical shape 132, a spheroid 133, an elongated cylinder 134, a proximally-increasing conical shape 135, a proximally-decreasing conical shape 136, or a diamond-like shape 137 with proximally and distally decreasing tapered conical portions. These shapes can be imparted to a mesh portion 102 by braiding the mesh portion 102 on a mandrel having the desired shapes (e.g., a mandrel with the same shape as the mesh shapes in FIG. 10) and then later heat set to impart the shape when expanded. Alternately, these shapes can be created by braiding the mesh 102 on a mandrel with a uniform consistent shape (e.g. cylindrical), heat setting the shape on the mandrel, removing the mesh portion 102, and then either tying off portions of the shape or placing marker bands selectively around portions of the shape to adopt the shapes shown in FIG. 10.

Previous embodiments discussed a core wire 104 which spanned the entirety of mesh portion 102, where the mesh portion sat directly over core wire 104. Alternative embodiments can utilize core wire 104 that terminates at a location proximal of the distal end of the mesh portion 102. This earlier termination point can provide the mesh portion a degree of independence to conform to the tortuous conditions of the vasculature to further aid in promoting full stent expansion.

For example, FIGS. 11, 12, 13, and 14 illustrate another embodiment of a stent assistance device 140 in which the core wire 104 terminates within mesh portion 102 or proximal to it. Looking to FIG. 11, the core wire 104 a core wire tip section 142 is located within the first, proximal-most bulb 102A. In one example, the core wire tip 142 can be platinum or tantalum wire coiled around either a nitinol wire or the distal end of the core wire 104. In another example, the core wire 104 terminates within the body of the pusher body 112, leaving only core wire tip 142 (e.g., coiled platinum or tantalum wire around a nitinol wire) exposed within the first, proximal-most bulb 102A. This tip section 142 can be seen in the magnified view of FIG. 13. The proximal end of mesh portion 102 is fixed directly to the body of pusher body 112 or immediately adjacent the body of pusher body 112 via proximal crimp point 108.

Figure 14:
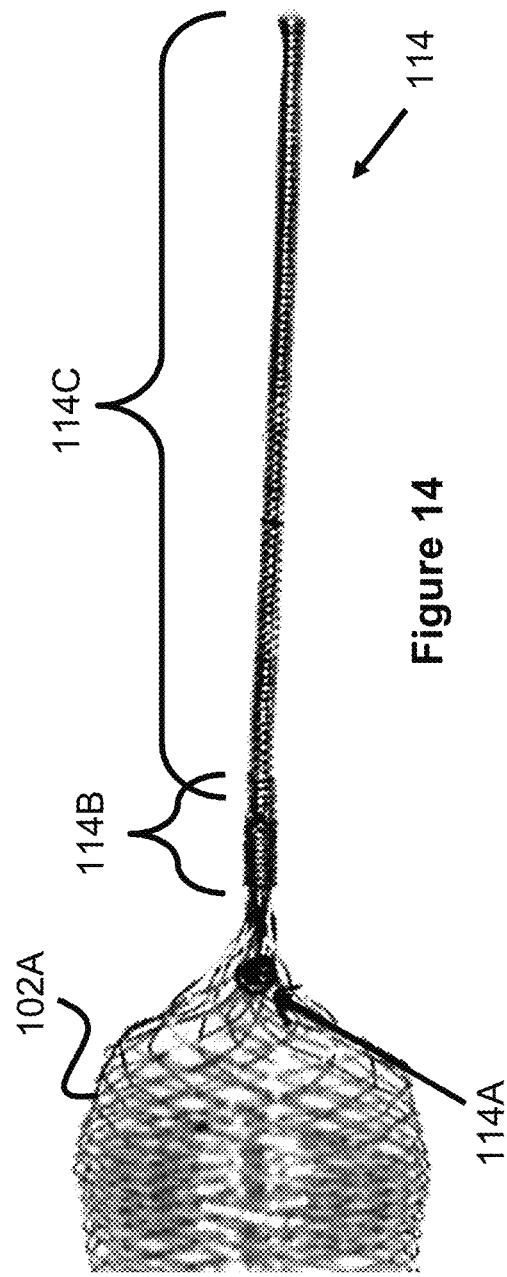
FIG. 14 illustrates a distal tip of the stent assistance device of FIG. 11, according to the present invention.

Optionally, the distal end of the mesh portion 102 may include a distal tip 114 connected to it, similar to previously described embodiments, in order to provide a guiding surface under the stent 12 as well as to provide a soft vessel contact surface to aid in placing the stent 12 without providing vessel trauma. As best seen in FIG. 14, the distal tip 114 includes an underlying nitinol wire that has a proximal laser-welded ball 114A within the distal-most mesh bulb 102A. A coil 114B of tantalum or platinum wire is wound over the nitinol wire and the distal-most portion of the mesh portion 102. A coil 114C of platinum or tantalum wire is also wound over the nitinol wire, being inter-wound with a portion of the tantalum/platinum coil 1146 and extending along the remaining distal length of the nitinol wire. Optionally, an adhesive or weld can be applied to the distal end of the tip 114. Additionally, portions of the underlying nitinol wire can be flattened or otherwise shaped.

Often, once a stent is deployed within a patient, thrombi can dislodge and move downstream, leading to further complications downstream in the vasculature. The following discussion are directed to embodiments that help collect or trap thrombi dislodged during a stent deployment procedure.

Figure 15:
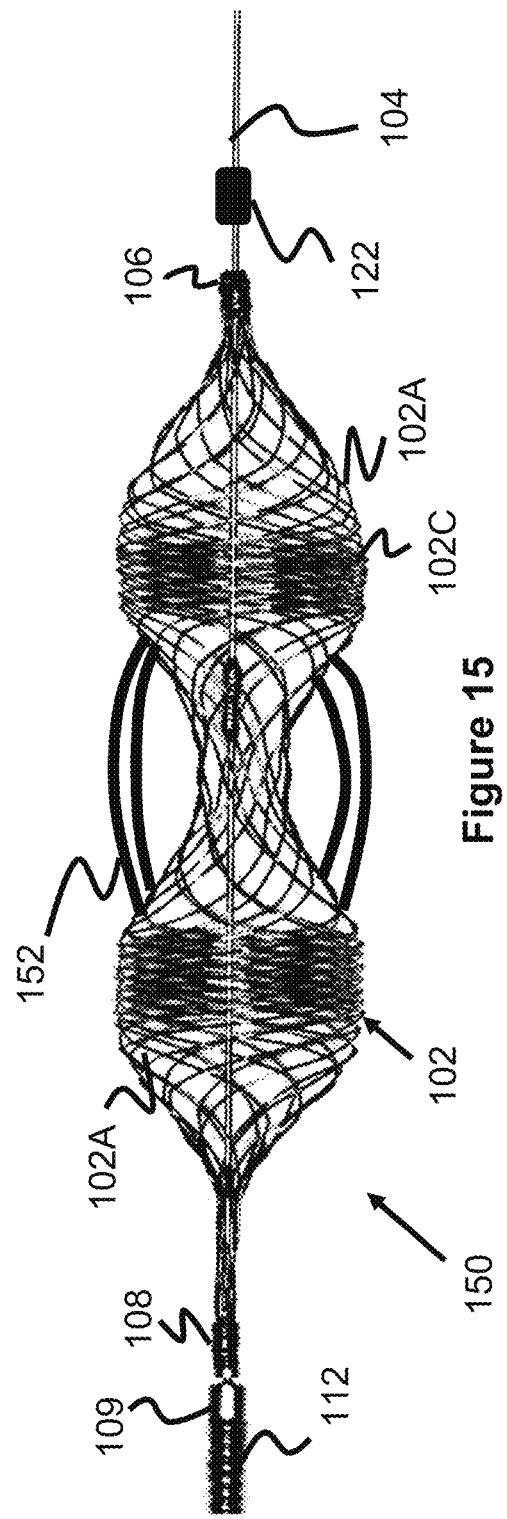
FIG. 15 illustrates a stent assistance device having wire frame members between bulbs, according to the present invention.

FIG. 15 illustrates an embodiment of a stent assistance device 150 utilizing mesh portion 102 where wire frame members 152 extend between the expanded bulbs 102A. These wire frame members 152 can provide further structural support to the bulbs 102A and can help catch/capture blood clots that may form during a procedure. These wire frame members 152 are preferably composed of wire that is the same diameter or larger than that making up the mesh portion 102 and are attached to either the wires of the mesh portion 102, to the underlying core wire 104, or a combination of each, such that the wire frame members 152 expand and contract with the mesh portion 102.

In one embodiment (shown in FIG. 15), four equidistant wire frame members 152 are used; each of which form an outwardly arced shape when expanded that are similar in diameter to the bulbs 102A. However, the wire frame members 152 can alternately have a spiral shape around the mesh portion 102, a linear shape between bulbs 102A, or similar geometric shapes.

FIGS. 16-17 show stent assistance device embodiments having a distal mesh element that captures dislodged thrombi. In FIG. 16, a stent assistance device 160 utilizes a mesh portion 102 having a relatively larger mesh bulb 162 that contains a concave filter 164 that acts as distal protection during a procedure, capturing blood clots, thrombus, or other debris that may be dislodged during the deployment of the stent 12. The concave filter 164 may be composed of a fine mesh, fabric, polymer film, or similar known filter materials. Additionally, other shapes of the filter 164 are also possible, such as a circular plane. The larger mesh bulb 162 can be woven from the wires of the mesh portion 102, forming an interconnected mesh structure. During a procedure, the mesh bulb 162 can be distally advanced past the stent 12 (or deployed prior to the stent 12) such that it is expanded prior to the stent 12 contacting the vessel.

Alternately, as seen in the device 166 in FIG. 17, the mesh bulb 162 can be fixed near a distal end of the core wire 104, separate from the mesh portion 102. This position may allow the physician to more easily deploy the bulb 162 and filter 164 prior to or at the very start of the deployment of the stent 12. This separate mesh bulb 162 can be configured to slide longitudinally on the core wire 104 or can be locked in place from sliding.

The embodiments disclosed herein have utilized a common delivery pusher body 112 used to deliver a stent 12 and a mesh portion 102. Other embodiments can utilize a stent 12 which is connected to a first, elongated delivery pusher that has a passage therethrough. A second pusher body 112 for the stent assistance device can be positioned within the first pusher, allowing the user to move the stent and stent assistance devices separately and independently.

It should be understood that the present invention is also directed to a kit comprising an introducer tube, a pusher body 112 disposed within the introducer tube, any of the stent assistance embodiments described in this specification attached to the pusher body 112, and a stent located near a distal end of the introducer tube and over a mesh portion 102 of the pusher body 112. In use, the physician can connect the introducer tube to the proximal hub of a catheter 14 and then advance the pusher (including the mesh portion 102) and the stent 12 into the catheter 14.

While the present invention has been described in terms of separate components, such as a pusher body 112, a core wire 104, and a mesh portion 102, it should be understood that one or more of these components may also be considered a pusher, a stent assistance system, or a stent assistance device.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A stent delivery device comprising:
   an elongated element; and
   a mesh portion having a compressed configuration and a radially-expanded configuration; and, a stent disposed over the mesh portion;
   wherein the mesh portion radially expands against an interior of the stent during deployment of the stent from a catheter to form, in its radially-expanded configuration, a bulb shape; and,
   wherein a distal end of the elongated element terminates within an interior of the bulb shape between a first end of the mesh portion and a second end of the mesh portion.

2. The stent delivery device of claim 1, wherein the bulb shape has a large diameter region, and adjoining smaller diameter regions on either side of the large diameter region.

3. The stent delivery device of claim 2, wherein the large diameter region is configured to contact a proximal portion of the stent.

4. The stent delivery device of claim 1, further comprising a pusher body.

5. The stent delivery device of claim 4, wherein the elongated element is attached to a distal end of the pusher body.

6. The stent delivery device of claim 4, wherein the elongated element extends distally from the pusher body.

7. The stent delivery device of claim 6, wherein a portion of the elongated element is positioned within a lumen of the pusher body.

8. The stent delivery device of claim 1, wherein the mesh portion is crimped to the elongated element.

9. The stent delivery device of claim 1, wherein the first end of the mesh portion is comprised of a proximal end of the mesh portion and wherein the second end of the mesh portion is comprised of a distal end of the mesh portion.

10. A stent delivery device comprising:
    an elongated element;
    a plurality of mesh bulbs including a first mesh bulb and a second mesh bulb disposed over the elongated element, each of the plurality of mesh bulbs having a compressed configuration and a radially-expanded configuration;
    wherein the second mesh bulb is spatially separated from the first mesh bulb in a proximal or distal direction by at least a portion of a length of the elongated element;
    a stent disposed over the plurality of mesh bulbs; and,
    wherein the plurality of mesh bulbs radially expand against an interior of the stent during deployment of the stent.

11. The stent delivery device of claim 10, wherein a distal end of the elongated element terminates within an interior of one of the plurality of mesh bulbs between a proximal end and a distal end of the plurality of mesh bulbs.

\* \* \* \* \*